(12) United States Patent
Fukuyama et al.

(10) Patent No.: US 8,780,350 B2
(45) Date of Patent: Jul. 15, 2014

(54) METHOD FOR MANUFACTURING ANODIZED ALUMINA, AND DEVICE AND METHOD FOR INSPECTING THE SAME

(71) Applicant: Mitsubishi Rayon Co., Ltd., Tokyo (JP)

(72) Inventors: Mitsufumi Fukuyama, Otake (JP); Yuji Matsubara, Otake (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 13/637,251

(22) Filed: Sep. 25, 2012

(65) Prior Publication Data

US 2013/0206601 A1 Aug. 15, 2013

Related U.S. Application Data

(63) Continuation-in-part of application No. PCT/JP2011/056865, filed on Mar. 22, 2011.

(30) Foreign Application Priority Data

Mar. 25, 2010 (JP) ................................. 2010-070279

(51) Int. Cl.

| | | |
|---|---|---|
| *G01N 21/25* | (2006.01) | |
| *C25D 11/24* | (2006.01) | |
| *G01B 11/25* | (2006.01) | |
| *C25D 11/04* | (2006.01) | |
| *C25D 11/12* | (2006.01) | |
| *G01N 21/956* | (2006.01) | |
| *G01B 11/24* | (2006.01) | |
| *C25D 11/16* | (2006.01) | |

(52) U.S. Cl.
CPC ................ *G01B 11/24* (2013.01); *C25D 11/24* (2013.01); *G01B 11/25* (2013.01); *C25D 11/045* (2013.01); *C25D 11/12* (2013.01); *G01N 21/95692* (2013.01); *C25D 11/16* (2013.01); *G01B 11/2509* (2013.01)
USPC .......................................................... 356/406

(58) Field of Classification Search
USPC .................................................. 356/402–425
See application file for complete search history.

(56) References Cited

U.S. PATENT DOCUMENTS

| | | | |
|---|---|---|---|
| 2004/0253624 A1* | 12/2004 | Smith et al. ........................ | 435/6 |
| 2005/0211566 A1* | 9/2005 | Tomita et al. ................. | 205/324 |
| 2009/0035450 A1 | 2/2009 | Tomaru | |

FOREIGN PATENT DOCUMENTS

JP 6-294634 A 10/1994

(Continued)

OTHER PUBLICATIONS

Zou Xiao, et al., "Preparartion and characteristics of Cu/AAO composite", School of Material Science and Engineering, vol. 41, No. 2. pp. 321-323, Tongi University, Shanghai 200092 (w/abstract).

*Primary Examiner* — Tarifur Chowdhury
*Assistant Examiner* — Abdullahi Nur
(74) *Attorney, Agent, or Firm* — Fitch, Even, Tabin & Flannery LLP

(57) ABSTRACT

The present invention relates to a method of manufacturing an article having a fine concave-convex structure on a surface thereof, the structure having pores in which a pore interval is less than or equal to a wavelength of visible light, including: irradiating a surface of the article having the fine concave-convex structure on the surface, with light from an illumination device; capturing an image of reflected light from the surface of the article having the fine concave-convex structure on the surface using imaging device; acquiring color information from an image captured by the imaging device; and inspecting the article having the fine concave-convex structure based on the color information. According to the present invention, it is possible to easily inspect the depth of the pores of anodized alumina and the pitch between the pores, and to provide a method of manufacturing anodized alumina having a stable pore shape.

21 Claims, 8 Drawing Sheets

(56) References Cited

FOREIGN PATENT DOCUMENTS

| JP | 09-101265 A | 4/1997 |
| JP | 2001-205327 A | 7/2001 |
| JP | 2005-156695 A | 6/2005 |
| JP | 2006-284569 A | 10/2006 |

OTHER PUBLICATIONS

Chinese Office Action dated Jul. 30, 2013, CN Application No. 201180015235.2.
International Search Report issued Jun. 28, 2011 in PCT Application PCT/JP2011/056865 (Japanese/Translation).
Written Opinion issued in PCT/JP2011/056865 (Japanese).

* cited by examiner

METHOD FOR MANUFACTURING ANODIZED ALUMINA, AND DEVICE AND METHOD FOR INSPECTING THE SAME

CROSS-REFERENCE TO RELATED APPLICATIONS

This Application is a U.S. continuation-in-part application of International Application PCT/JP2011/056865, filed Mar. 22, 2011, designating the United States, which claims priority from Japanese Patent Application 2010-070279, filed Mar. 25, 2010, the complete disclosures of which are hereby incorporated herein by reference in their entirety for all purposes.

TECHNICAL FIELD

The present invention relates to a method of manufacturing anodized alumina (porous oxide film) having two or more pores formed on the surface of an aluminum substrate, and a method and device for inspecting the same.

Priority is claimed on Japanese Patent Application No. 2010-070279, filed Mar. 25, 2010, the content of which is incorporated herein by reference.

This application is a continuation-in-part application based on PCT/JP2011/056865, filed Mar. 22, 2011. This international application was published in Japanese on Sep. 29, 2011 as PCT International Publication No. WO2011/118596.

BACKGROUND ART

Articles having a fine concave-convex structure with a pitch less than or equal to the wavelength of visible light on a surface thereof, express an anti-reflective function or the like, and thus the usefulness thereof is currently attracting attention. Particularly, a fine concave-convex structure called a Moth-Eye structure has been known to express an effective anti-reflective function due to a continuous increase from the refractive index of the air to the refractive index of a material.

As methods of manufacturing an article having a fine concave-convex structure on a surface thereof, the following methods, (i) or (ii), are known, and the method of (ii) is excellent from the viewpoint of productivity and economic efficiency.

(i) A method of manufacturing an article having a fine concave-convex structure on the surface thereof by directly processing a surface such as a transparent substrate.

(ii) A method of transferring an inversion structure onto a surface such as a transparent substrate using a mold having an inversion structure corresponding to a fine concave-convex structure.

As a method of forming an inversion structure in a mold, an electron beam lithography method, a laser light interference method and the like are known. In recent years, as a method in which an inversion structure is capable of being formed more easily, a method of anodizing a surface of an aluminum substrate has attracted attention (see, for example, PTL 1).

Anodized alumina formed by anodizing the surface of the aluminum substrate is an aluminum oxide film (alumite), and has a fine concave-convex structure composed of two or more pores in which the pitch is less than or equal to the wavelength of visible light.

In the above-mentioned anodized alumina, when non-uniformity occurs in the concentration or the temperature of an electrolyte for immersing the aluminum substrate at the time of anodization, or non-uniformity occurs in the surface texture of the aluminum substrate, a slight non-uniformity may occur in the depth of the pores and the pitch between the pores. When the area of a region in which the depth of the pores of the anodized alumina and the pitch between the pores are not formed as designed is increased, such a mold is not able to be used in manufacturing an article having a fine concave-convex structure on the surface thereof. However, a method in which the depth of the pore of anodized alumina and the pitch between the pores can be easily inspected has not been available.

In addition, a mold release agent is attached to the surface of a mold including an anodized alumina layer having such a fine concave-convex structure in order to enhance the mold releasability of a molded article. When an excessive amount of mold release agent is attached to the surface of the anodized alumina layer having a fine concave-convex structure, the fine concave-convex structure is buried by the mold release agent, and thus a problem occurs in that an optimum fine concave-convex structure is not transferred onto the surface such as a transparent substrate. On the other hand, when the amount of the mold release agent is extremely small, desired mold releasability is not obtained, and thus a problem occurs. For this reason, it is necessary to perceive the attachment state of the mold release agent on the surface of the anodized alumina layer having a fine concave-convex structure, but there is a problem in that currently, there is not a method for easily inspecting the attachment state of the mold release agent on the surface of anodized alumina.

In addition, although such a mold, which makes use of the anodized alumina, is manufactured by anodizing the aluminum substrate, a material used in the aluminum substrate serving as a material of the anodized alumina is of a high purity. However, the crystal grains of high-purity aluminum used for manufacturing the high-purity aluminum substrate have a tendency to be coarsened due to casting or the like, and coarse crystal grains that can even be seen with the naked eye are generated in the aluminum substrate. For this reason, there is a problem in that the same grain boundary pattern is generated even in the surface of the anodized alumina of the mold manufactured using such an aluminum substrate, and such a grain boundary pattern is even transferred onto the surface of an article such as an optical sheet manufactured using this mold.

Consequently, in order to make a pattern caused by the crystal grains refined and uniform, the aluminum substrate is manufactured by rolling, extruding, forging, or the like. However, even when such processes are performed, the traces of the coarse crystal grains at the time of casting before forging cause non-uniformity in the crystal orientation depending on the conditions of the processing direction, the number of repetitions or the like, and thus remain in the aluminum substrate. The cicatrix thereof may remain in the mold having a fine concave-convex structure processed from the aluminum substrate, as a flow pattern which is difficult to visually recognize with the naked eye. This flow pattern is difficult to visually recognize on the mold. However, when optical sheet and the like are manufactured using the mold, the flow pattern is transferred onto the optical sheet as a flow pattern (in which a mark of a liquid flow remains) such as marbling on the sheet surface which is visible to the naked eye, which results in an appearance defect.

The optical sheet onto which the fine concave-convex structure of anodized porous alumina is transferred has excellent anti-reflection performance. Therefore, when the optical sheet is attached to the surface of an electronic display device and a dark image is displayed, the difference in reflectance or transmittance of slight light tends to be conspicuously visually recognized as a defect. For this reason, non-uniformity of the surface of the aluminum substrate in the crystal orientation which is not visually recognized on the mold is transferred onto the optical sheet as a defect and tends to be conspicuously visually recognized.

Further, there is a problem in that there is no method capable of easily inspecting the flow pattern of the mold having an anodized alumina layer formed by anodization on the surface thereof.

CITATION LIST

Patent Literature

[PTL 1] Japanese Laid-Open Patent Application No. 2005-156695

DISCLOSURE OF INVENTION

Problems to be Solved by the Invention

According to one aspect the present invention, there is provided a method which is capable of easily inspecting the depth of pores of anodized alumina and the pitch between the pores, and manufacturing anodized alumina having a stable pore shape. In addition, according to another aspect of the present invention, there is provided an inspection device and an inspection method which are capable of easily inspecting the attachment state of a mold release agent to the surface of anodized alumina having the mold release agent attached to the surface thereof, and a method of manufacturing a member having anodized alumina on the surface thereof in which the attachment non-uniformity of the mold release agent is suppressed and to which the mold release agent is properly attached. In addition, according to another aspect of the present invention, there is provided an inspection device and an inspection method which are capable of easily inspecting a flow pattern of a member having a fine concave-convex structure manufactured by anodizing an aluminum substrate, and a member in which the generation of a flow pattern is suppressed.

Means for Solving the Problem

The inventor has found, as a result of keen examination in view of the above-mentioned problems, that the color of reflected light from anodized alumina varies with the pore aspect ratio (depth/pitch) of the anodized alumina, and thus has completed the present invention.

The color of reflected light of the anodized alumina is not only an interference color of a general thin film as seen in a soap bubble, but also a color influenced by a structure of the depth or pitch of pores of anodized alumina.

Further, the inventor has found, as a result of keen examination, that the color of light reflected from the surface of a mold having an anodized alumina layer on the surface thereof varies with the state of a mold release agent attached to a fine concave-convex structure, and a flow pattern of the mold. That is, the inventor has found that the color of light reflected from anodized alumina is influenced by the shape of the fine concave-convex structure of the anodized alumina or the thickness of the anodized alumina, the state of the mold release agent attached to the surface, and the flow pattern of the mold.

That is, the present invention relates to the following.

(1) A method of manufacturing an article having a fine concave-convex structure on a surface thereof, the structure having two or more pores in which a pore interval is less than or equal to a wavelength of visible light, including:

irradiating a surface of the article having the fine concave-convex structure on the surface thereof, with light from an illumination device after the fine concave-convex structure is formed;

capturing an image of reflected light from the surface of the article having the fine concave-convex structure on the surface using an imaging device;

acquiring color information from an image captured by the imaging device; and inspecting the article having the fine concave-convex structure on the surface based on the color information.

(2) The method of manufacturing an article having a fine concave-convex structure on a surface thereof according to the above (1), wherein in the capturing the image of the reflected light from the surface of the article having the fine concave-convex structure on the surface using the imaging device, an angle of an optical axis of the imaging device is 45 to 89.9 degrees with respect to a normal line of the surface of anodized alumina.

(3) The method of manufacturing anodized alumina according to the above (1), wherein in the capturing the image of the reflected light from the surface of the article having the fine concave-convex structure on the surface using the imaging device, the angle of the optical axis of the imaging device is 65 to 89.9 degrees with respect to the normal line of the surface of anodized alumina.

(4) The method of manufacturing an article having a fine concave-convex structure on a surface thereof according to the above (1), wherein in the capturing the image of the reflected light from the surface of the article having the fine concave-convex structure on the surface using the imaging device, an angle of an optical axis of the imaging device is 80 to 89.9 degrees with respect to a normal line of the surface of anodized alumina.

(5) The method of manufacturing an article having a fine concave-convex structure on a surface thereof according to the above (1), further including inspecting a shape of the pore based on the color information.

(6) The method of manufacturing an article having a fine concave-convex structure on a surface thereof according to the above (1), further including inspecting a mold release agent attached to the fine concave-convex structure based on the color information.

(7) The method of manufacturing an article having a fine concave-convex structure on a surface thereof according to the above (1), further including inspecting a flow pattern of the article having the fine concave-convex structure on the surface based on the color information.

(8) The method of manufacturing an article having a fine concave-convex structure on a surface thereof according to the above (1), wherein the inspecting of the article having the fine concave-convex structure on the surface based on the color information includes capturing an image of reflected light from the article having the fine concave-convex structure on the surface as an RGB signal, and inspecting the article having the fine concave-convex structure on the surface based on information of the RGB signal.

(9) The method of manufacturing an article having a fine concave-convex structure on a surface thereof according to the above (1), wherein the inspecting of the article having the fine concave-convex structure on the surface based on the color information includes capturing reflected light from the article having the fine concave-convex structure on the surface as an RGB signal, converting the RGB signal into an HSL color coordinate system, and inspecting the article having the fine concave-convex structure on the surface based on information of the HSL color coordinate system.

(10) The method of manufacturing an article having a fine concave-convex structure on a surface thereof according to the above (1), wherein the article having the fine concave-convex structure on the surface is an article having anodized alumina on the surface.

(11) The method of manufacturing an article having a fine concave-convex structure on a surface thereof according to the above (1), further including the following steps (a) to (e) before irradiating the surface of the article having the fine concave-convex structure on the surface thereof with light from the illumination device:

(a) a step of anodizing a surface of a mirror-finished aluminum substrate in an electrolyte at a constant voltage, and forming an oxide film on the surface;

(b) a step of removing at least a portion of the oxide film, and forming a pore originating point of anodization on the surface of the aluminum substrate;

(c) a step of re-anodizing the surface of the aluminum substrate, on which the pore originating point is formed, in an electrolyte at a constant voltage, and forming an oxide film having a pore corresponding to the pore originating point on the surface;

(d) a step of expanding a diameter of the pore; and (e) a step of repeatedly performing the step (c) and the step (d).

(12) A method of manufacturing an optical film, including transferring the fine concave-convex structure of the article manufactured by the manufacturing method according to the above (1) to manufacture the optical film.

(13) A device of inspecting an article having a fine concave-convex structure on a surface thereof, the structure having two or more pores in which a pore interval is less than or equal to a wavelength of visible light, including:

an illumination device that irradiates the surface of the article having the fine concave-convex structure on the surface with light;

an imaging device that captures an image reflected light from the surface of the article having the fine concave-convex structure on the surface; and an image processor that determines a quality of the article having the fine concave-convex structure on the surface based on color information obtained from the image captured by the imaging device.

(14) The device of inspecting an article according to the above (13), wherein in the imaging device that captures an image of reflected light from the surface of the article having the fine concave-convex structure on the surface, an angle of an optical axis of the imaging device is 45 to 89.9 degrees with respect to a normal line of the surface of anodized alumina.

(15) The device of inspecting an article according to the above (13), wherein in the imaging device that captures an image of reflected light from the surface of the article having the fine concave-convex structure on the surface, an angle of an optical axis of the imaging device is 65 to 89.9 degrees with respect to a normal line of the surface of anodized alumina.

(16) The device of inspecting an article according to the above (13), wherein in the imaging device that captures an image of reflected light from the surface of the article having the fine concave-convex structure on the surface, an angle of an optical axis of the imaging device is 80 to 89.9 degrees with respect to a normal line of the surface of anodized alumina.

(17) The device of inspecting an article according to the above (13), wherein the image processor inspects a shape of the pore based on the color information.

(18) The device of inspecting an article according to the above (13), wherein the image processor inspects a mold release agent attached to the fine concave-convex structure based on the color information.

(19) The device of inspecting an article according to the above (13), wherein the image processor inspects a flow pattern of the article having the fine concave-convex structure on the surface based on the color information.

Effects of the Invention

According to the anodized alumina manufacturing method, inspection device and inspection method of the present invention, it is possible to easily inspect the shape of a fine concave-convex structure of the depth of pores of anodized alumina and the pitch between the pores, the state of a mold release agent attached to the fine concave-convex structure, and the flow pattern of a mold, and to manufacture anodized alumina having a stable pore shape.

EMBODIMENTS OF THE INVENTION

Inspection Device

Figure 1:
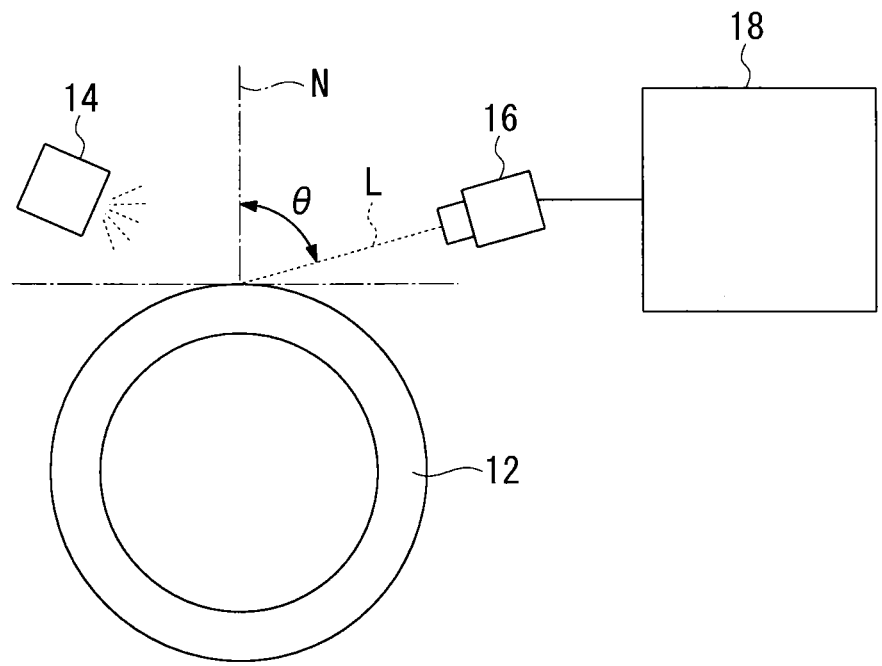
FIG. 1 is a schematic configuration diagram illustrating an example of an inspection device of anodized alumina according to the present invention.

FIG. 1 is a schematic configuration diagram illustrating an example of an inspection device of anodized alumina according to the present invention.

The inspection device includes rotation means (not shown) that rotate a roll-shaped mold 12 in which anodized alumina having two or more pores is formed on the surface of a roll-shaped aluminum substrate, a linear illumination device 14 (illumination means or illumination device) that linearly irradiates the mold 12 with light, a color line CCD camera 16 (imaging means or imaging device) that captures an image of reflected light from the surface of the anodized alumina of the mold 12, and an image processor 18 (image processing means or image processor) that processes an image signal from the color line CCD camera 16.

The linear illumination device 14 is disposed so that the longitudinal direction of the irradiation range of the mold 12 with light is at right angles to the circumferential direction (rotational direction) of the mold 12.

The linear illumination device 14 includes a high-frequency lighting fluorescent lamp lighting device, a rod illumination device, a linearly disposed optical fiber illumination device, and an LED illumination device and the like.

In addition, the illumination device is not limited to a linear illumination device, but may be a planar illumination device, or a spot illumination device.

The color line CCD camera 16 is a camera in which two or more color CCD elements are disposed one-dimensionally, and has a function of receiving light emitted from the linear illumination device 14 and reflected from the surface of the anodized alumina of the mold 12 with the color CCD elements and outputting an image signal of RGB for each pixel.

The color line CCD camera 16 is disposed so that the longitudinal direction of the imaging range is at right angles to the circumferential direction (rotational direction) of the mold 12. In addition, the color line CCD camera 16 is preferably disposed so that the angle θ of an optical axis L of the color line CCD camera 16 is 45 to 89.9 degrees with respect to a normal line N of the surface (tangent plane) of the anodized alumina of the mold 12 which is within the imaging range. When the angle θ is greater than or equal to 45 degrees, the color of reflected light on the surface of the anodized alumina which corresponds to the pore aspect ratio (depth/pitch) of the anodized alumina appears clearly. When the angle θ is greater than or equal to 65 degrees, it is not as easily influenced by noise as when the angle θ is 45 degrees. The angle θ is more preferably greater than or equal to 80 degrees and the angle θ is much more preferably greater than or equal to 85 degrees. When the angle θ exceeds 89.9 degrees, imaging is difficult.

The angle θ is preferably 45 degrees to 89.9 degrees, more preferably 65 degrees to 89.9 degrees, much more preferably 80 degrees to 89.9 degrees, and particularly preferably 85 degrees to 89.9 degrees.

The image processor 18 is a processor which acquires an image signal of 256-gradation RGB for each pixel which is output from the color line CCD camera 16 and determines whether the pore aspect ratio (depth/pitch) of the anodized alumina is within a predetermined range based on the acquired image signal.

In addition, for the purpose of simplification of the determination, the image signal of RGB is converted into an HSL color coordinate system, and it can also be determined whether the pore aspect ratio (depth/pitch) of the anodized alumina is within a predetermined range based on digital information of the gradated hue (H).

The predetermined range of the aspect ratio (depth/pitch) can be set arbitrarily, is preferably 0.5 to 4.0, more preferably 1.0 to 3.5, much more preferably 1.8 to 3.5, and most preferably 2.0 to 3.0.

At the time of determination, specifically, when NG pixels, which are out of the range of gradation at which the color gradation is set in advance, are extracted, and the ratio of the NG pixels in a predetermined region (for example, 2,000×4,000 pixels) exceeds a predetermined ratio (for example, 5%), or the like, the mold 12 to be inspected is determined to be a defective product.

For example, when the determination is performed on the image signal of RGB, the following process is performed.

When the depth of the pores of the anodized alumina of the mold 12 and the pitch between the pores are designed to be 200 nm and 100 nm (aspect ratio of 2), respectively, and the anodized alumina is formed as designed, measurement of the color of reflected light of the anodized alumina results in values of R: 190, G: 160, and B: 120. Thus, the color range in a non-defective mold 12 is set as no more than ±10, for example, in any of RGB.

In addition, when the determination is performed on the HSL color coordinate system, the following process is performed, for example.

When the depth of the pores of the anodized alumina of the mold 12 and the pitch between the pores are designed to be 200 nm and 100 nm (aspect ratio of 2), respectively, and the anodized alumina as designed is formed, measurement of the hue (H) of reflected light of the anodized alumina results in light red (H=24 or so). Thus, the range of gradation of the hue (H) in the non-defective mold 12 is set to, for example, 14 to 34.

On the other hand, when the depth of the pores of the anodized alumina of the mold 12 and the pitch between the pores are designed to be 100 nm and 100 nm (aspect ratio of 1), respectively, and anodized alumina is formed as designed, the measurement of the hue (H) of reflected light of the anodized alumina causes light green (H=51 or so) to be obtained. Similarly, when the depth of the pores of the anodized alumina of the mold 12 and the pitch between the pores are designed to be 200 nm and 200 nm (aspect ratio of 1), respectively, and the anodized alumina as designed is formed, the measurement of the hue (H) of reflected light of the anodized alumina causes light yellow (H=38 or so) to be obtained. Thus, the gradation of the hue (H) of pixels corresponding to a portion in which the anodized alumina is not formed as designed is out of the gradation range (for example, H=14 to 34) which is set in advance.

Additionally, means for performing HSL conversion and determination may be realized using dedicated hardware. In addition, the means for performing HSL conversion and determination may be constituted by at least a memory and a central processing unit (CPU), and may load a program for realizing a function of HSL conversion and determination into the memory and execute the program, to thereby realize the function.

In addition, an input device, a display device and the like are connected to the image processor as peripheral equipment. Herein, the input device is can be an input device such as a display touch panel, a switch panel, or a keyboard, and the display device can be as a CRT, a liquid crystal display device and the like.

Inspection Method

A method of inspecting anodized alumina using the inspection device shown in FIG. 1 will be described below.

First, the surface of the roll-shaped aluminum substrate is anodized under such conditions that the depth of the pores of the anodized alumina and the pitch between the pores are set to 200 nm and 100 nm (aspect ratio of 2), respectively, and the mold 12 is obtained.

The mold 12 is attached to rotation means, and the surface of the anodized alumina of the rotating roll-shaped mold 12 is irradiated with light from the linear illumination device 14.

The image of reflected light from the surface of the anodized alumina is captured by the color line CCD camera 16.

Regarding the image of a circumference of the surface of the anodized alumina of the mold 12 which is output from the color line CCD camera 16, the image signal of RGB is converted into the HSL color coordinate system for each pixel, as necessary, in the image processor 18, and digital information of the color (hue (H)) expressed as 256 gradations is obtained.

In the image processor 18, when NG pixels which are out of the range of gradation (for example, H=14 to 34) of which the gradation of the hue (H) is set in advance are extracted from the image of a circumference of the surface of the anodized alumina of the mold 12, and the ratio of the NG pixels in a predetermined region (for example, 2,000×4,000 pixels) exceeds a predetermined ratio (for example, 5%), or the like, the mold 12 to be inspected is determined to be a defective product.

In the anodized alumina inspection device according to the present invention described above and the method of inspecting the same, it is possible to estimate whether the pore aspect ratio of the anodized alumina is formed as designed using a variation of the color of reflected light on the surface of the anodized alumina in accordance with the pore aspect ratio (depth/pitch) of the anodized alumina, and thus whether the depth of the pores of the anodized alumina and the pitch between the pores are formed as designed can be easily inspected, for example, compared with a method of measuring the depth of the pores and the pitch between the pores through cross-sectional observation of the anodized alumina using an electron microscope.

Additionally, the device of inspecting anodized alumina according to the present invention may preferably includes illumination means (illumination device) for irradiating the surface of the anodized alumina with light, imaging means (imaging device) for capturing an image of reflected light from the surface of the anodized alumina, and image processing means (image processor) for determining whether the pore aspect ratio (depth/pitch) of the anodized alumina is within a predetermined range based on color information obtained from the image captured by the imaging device, and is not limited to the example shown.

Figure 2:
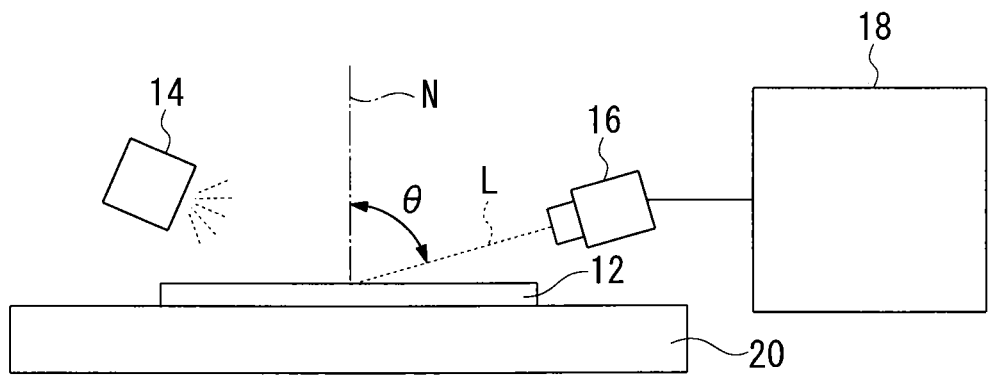
FIG. 2 is a schematic configuration diagram illustrating another example of the inspection device of the anodized alumina according to the present invention.

For example, as shown in FIG. 2, the above-mentioned device may be an inspection device that performs inspection of the plate-shaped mold 12 moving in the horizontal direction using movement means 20.

In addition, a method of determining that the mold 12 to be inspected is a defective product is also not limited to the above-mentioned method.

In addition, the imaging device also uses the color line CCD camera as mentioned above, but may be configured such that a monochrome line CCD camera and a color filter are combined, and may be configured such that a portion of data taken by an area CCD is extracted and data is reconstructed as taken by a line CCD. In addition, the above-mentioned device may be an inspection device that measures a reflection spectrum using a photo-detector and determining a non-defective product and a defective product from the reflection spectrum.

In addition, in the method of processing an image signal in the image processor, the process is performed using a 256-gradation image signal. However, the image signal may be used so that a normal portion and an abnormal portion can be determined from the image signal, and thus may be a 512-gradation signal, a 1,024-gradation signal, or an analog signal.

Manufacturing Method

Hereinafter, a description will be made of a mold in which anodized alumina having two or more pores in which the pitch is less than or equal to the wavelength of visible light is formed on the surface by anodizing the surface of the aluminum substrate.

Examples of the method of manufacturing a mold include forming anodized alumina having two or more pores (concave portion) on the surface of the substrate including aluminum.

As a method of manufacturing the mold, a method of performing the following steps in order is preferable.

First Oxide Film Forming Step (a):

The surface of a mirror-finished aluminum substrate is anodized in an electrolyte at a constant voltage, and an oxide film is formed on the surface (hereinafter, also referred to as step (a)).

Oxide Film Removal Step (b):

At least of a portion of the oxide film is removed, and a pore originating point of anodization is formed on the surface of the aluminum substrate (hereinafter, also referred to as step (b)).

Second Oxide Film Forming Step (c):

The surface of the aluminum substrate on which the pore originating point is formed is re-anodized in an electrolyte at a constant voltage, and an oxide film having a pore corresponding to the pore originating point is formed on the surface (hereinafter, also referred to as step (c)).

Pore Diameter Expansion Step (d):

The diameter of the pore is expanded (hereinafter, also referred to as step (d)).

Repetition Step (e):

The second oxide film forming step (c) and the pore diameter expansion step (d) are repeatedly performed as necessary (hereinafter, also referred to as step (e)).

According to the method including steps (a) to (e), a taper-shaped pore of which the diameter is gradually reduced in the depth direction from an opening is periodically formed on the surface of the mirror-finished aluminum substrate. As a result, it is possible to obtain a mold in which anodized alumina having two or more pores is formed on the surface.

Before step (a), preprocessing of removing the oxide film on the surface of the aluminum substrate may be performed. A method of removing the oxide film includes a method of immersing the oxide film in a chromic acid/phosphoric acid mixture, or the like.

In addition, regularity of an array of the pores slightly decreases, but step (c) and the following may be performed without performing step (a) depending on the application of a material to which the surface of the mold is transferred.

Hereinafter, each step will be described in detail.

Figure 3:
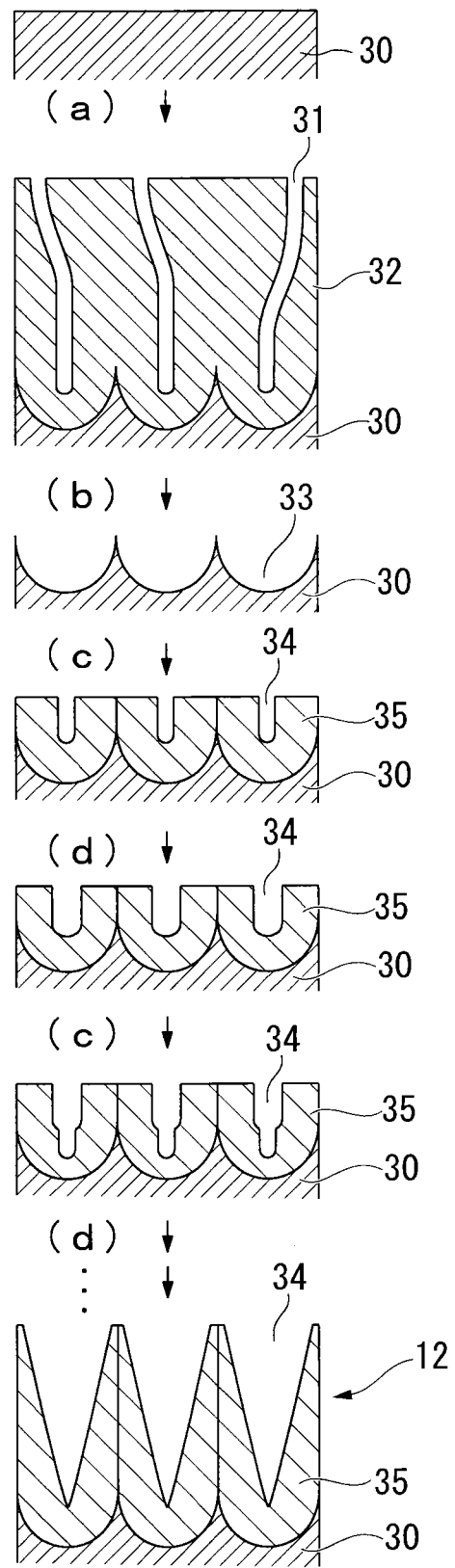
FIG. 3 is a cross-sectional view illustrating a process of manufacturing a mold having the anodized alumina on the surface thereof.

Step (a):

In the first oxide film forming step (a), the surface of the mirror-finished aluminum substrate is anodized in an electrolyte at a constant voltage, and as shown in FIG. 3, an oxide film 32 having pores 31 is formed on the surface of an aluminum substrate 30.

The electrolyte includes an acid electrolyte and an alkaline electrolyte, and the acid electrolyte is preferable.

The acid electrolyte includes oxalic acid, sulfuric acid, a mixture thereof, and the like.

When oxalic acid is used as an electrolyte, the concentration of the oxalic acid is preferably less than or equal to 0.7 M. When the concentration of the oxalic acid exceeds 0.7 M, the current value at the time of anodization becomes too high and thus the surface of the oxide film may become coarse.

In addition, the voltage at the time of anodization is set to 30 to 60 V, thereby allowing a mold in which anodized alumina with pores having a high regularity of which the pitch is approximately 100 nm is formed on the surface to be obtained. The regularity tends to decrease even when the voltage at the time of anodization is higher or lower than this range, and thus the pitch may become larger than the wavelength of visible light.

The temperature of the electrolyte is preferably less than or equal to 60° C., and more preferably less than or equal to 45° C. When the temperature of the electrolyte exceeds 60° C., a phenomenon referred to as "burning" tends to occur, and thus the pores may be broken, or the regularity of the pores may be disturbed due to melting of the surface.

When sulfuric acid is used as an electrolyte, the concentration of the sulfuric acid is preferably less than or equal to 0.7 M. When the concentration of the sulfuric acid exceeds 0.7 M, the current value at the time of anodization becomes too high and thus the constant voltage may be able to be maintained.

In addition, the voltage at the time of anodization is set to 25 to 30 V, thereby allowing a mold in which anodized alumina with pores having a high regularity of which the pitch is approximately 63 nm is formed on the surface to be obtained. The regularity tends to decrease even when the voltage at the time of anodization is higher or lower than this range, and the pitch may become larger than the wavelength of visible light.

The temperature of the electrolyte is preferably less than or equal to 30° C., and more preferably less than or equal to 20° C. When the temperature of the electrolyte exceeds 30° C., a phenomenon referred to as "burning" tends to occur, the pores may be broken, or the regularity of the pores may be disturbed due to melting of the surface.

In step (a), the oxide film formed by performing anodization for a long period of time becomes thick, and thus the regularity of an array of the pores can be improved. However, at this time, a macro-concave-convex due to the crystal grain boundary is further suppressed by setting the thickness of the oxide film to less than or equal to 30 µm, and thus a mold more suitable for manufacturing an article for optics application can be obtained. The thickness of the oxide film is more preferably 1 to 10 µm, and much more preferably 1 to 3 µm. The thickness of the oxide film can be observed using a field emission-type scanning electron microscope or the like.

Step (b):

After step (a), the oxide film 32 formed through step (a) is removed, thereby allowing periodic depressions corresponding to the bottom (called a barrier layer) of the removed oxide film 32, that is, pore originating points 33 to be formed, as shown in FIG. 3.

The formed oxide film 32 is first removed, and the pore originating points 33 of anodization are formed, thereby allowing the regularity of the pores to be improved (see, for example, "Applied Physics" Mashita, 2000, Vol. 69, No. 5, p. 558). Additionally, when the pores are not required to have a high regularity, the oxide film 32 may be completely removed in step (b), and at least a portion thereof may be removed.

A method of removing the oxide film 32 includes a method of removing the oxide film using a solution for selectively dissolving alumina without dissolving aluminum. Such a solution includes, for example, a chromic acid/phosphoric acid mixture or the like.

Step (c):

The aluminum substrate 30 on which the pore originating points 33 are formed is re-anodized in an electrolyte at a constant voltage, and an oxide film is formed again.

In step (c), anodization may be performed under the conditions (electrolyte concentration, electrolyte temperature, formation voltage and the like) similar to step (a).

Thereby, as shown in FIG. 3, an oxide film 35 in which columnar pores 34 are formed can be formed. In step (c), as anodization is performed for a long period of time, deeper pores can be obtained. However, for example, when a mold for manufacturing an optical article such as an anti-reflective article is manufactured, an oxide film of approximately 0.01 to 0.5 µm may be formed herein, and it is not necessary to form an oxide film having a thickness to be formed in step (a).

Step (d):

After step (c), the pore diameter expansion step of expanding the diameter of the pore 34 formed in step (c) is performed, and the diameter of the pore 34 is expanded as shown in FIG. 3.

A specific method of the pore diameter expansion includes a method of performing immersion in a solution for dissolving alumina, and expanding the diameter of the pore formed in step (c) by etching. Such a solution includes, for example, a phosphoric acid aqueous solution of approximately 5% by mass, or the like. As the time of step (d) is lengthened, the diameter of the pore becomes larger.

Step (e):

Step (c) is performed again, and the pore 34 is formed in a two-tier columnar shape having a different diameter as shown in FIG. 3. After that, step (d) is performed again. As shown in FIG. 3, the pore 34 can be formed in a taper shape of which the diameter is gradually reduced in the depth direction from the opening through the repetition step (e) in which step (c) and step (d) are repeated in this manner. As a result, it is possible to obtain the mold 12 in which anodized alumina having two or more periodic pores is formed on the surface.

A pore having various shapes can be formed by appropriately setting the conditions of step (c) and step (d), for example, the time of anodization and the time of the pore diameter expansion. Thus, such conditions may be appropriately set in accordance with the application of an article to be manufactured using the mold. In addition, when this mold is used for manufacturing an anti-reflective article such as an anti-reflective film, the pitch and the depth of the pores can be arbitrarily changed by appropriately setting such conditions, and thus an optimum refractive index variation can also be designed.

The mold manufactured in this manner has a fine concave-convex structure on the surface thereof, as a result of formation of a lot of periodic pores. When the pitch of the pores in this fine concave-convex structure is less than or equal to the wavelength of visible light, that is, less than or equal to 400 nm, a so-called moth-eye structure is formed.

The pitch is a distance from the center of the concave portion (pore) of the fine concave-convex structure to the center of the concave portion (pore) adjacent thereto.

When the pitch is larger than 400 nm, scattering of visible light occurs, and thus a sufficient anti-reflective function is not expressed, which leads to unsuitableness for manufacturing an anti-reflective article such as an anti-reflective film.

The pitch is preferably 50 to 400 nm, more preferably 70 to 300 nm, and much more preferably 80 to 250 nm.

When the mold is used for manufacturing an anti-reflective article such as an anti-reflective film, the pitch of the pores is less than or equal to the wavelength of visible light, and the depth of the pores is preferably greater than or equal to 50 nm, and more preferably greater than or equal to 100 nm.

The depth is a distance from the opening of the concave portion (pore) of the fine concave-convex structure to the innermost portion thereof.

When the depth of the pore is greater than or equal to 50 nm, the reflectance of the surface of an article for optics application formed by a transfer of the surface of the mold, that is, the transfer surface decreases.

In addition, the pore aspect ratio (depth/pitch) of the mold is preferably 1.0 to 4.0, more preferably 1.3 to 3.5, much more preferably 1.8 to 3.5, and most preferably 2.0 to 3.0. When the aspect ratio is greater than or equal to 1.0, the transfer surface having a low reflectance can be formed, and thus the incident angle dependence or the wavelength dependence also becomes sufficiently lower. When the aspect ratio is greater than 4.0, the mechanical strength of the transfer surface tends to decrease.

The shape of the mold may be plate-like, and may be roll-like.

On the surface on which the fine concave-convex structure of the mold is formed, mold releasing may be performed so that mold release is facilitated. A mold releasing method includes, for example, a method of coating silicon-based polymer or fluoropolymer, a method of evaporating a fluorine compound, a method of coating a fluorine-based or fluorine silicon-based silane coupling agent, or the like.

Regarding the mold manufactured as mentioned above, the image of reflected light from the surface of the anodized alumina is captured by the color line CCD camera 16, using the inspection device shown in FIG. 2 when the mold is plate-like and using the inspection device shown in FIG. 1 when the mold is roll-like.

Regarding the image on the surface of the anodized alumina of the mold 12 which is output from the color line CCD camera 16, the image signal of RGB is converted into the HSL color coordinate system for each pixel, as necessary, in the image processor 18, and information of the color (hue (H)) is obtained.

The quality of the mold 12 is determined from the acquired color information, and the mold 12 is advanced to the step of manufacturing an article having a fine concave-convex structure on the surface thereof, and the like, when it is determined to be good. When there is, as a defective product, a uniform defect throughout the entire mold, a defect in which the depth of the nanohole pore is deep or is shallow overall, or a defect in which the pitch of nanohole pores is wide or narrow overall, any of the above-mentioned anodization steps (a) to (e) are performed on the mold 12 again, and the anodized alumina is restored. When there is a defect in which restoration cannot be made only by any execution of the above-mentioned anodization steps (a) to (e) due to the existence of the abnormal nanohole shape in part of the mold, the above-mentioned anodization steps (a) to (e) may be performed from the beginning by removing an anodized alumina layer for each aluminum substrate. The anodized alumina is formed again and then is inspected again, and the anodization step and the inspection step are repeatedly performed until the mold 12 becomes non-defective.

In addition, the presence or absence of a flow pattern of the mold 12 can be inspected from the acquired color information. In the inspection of the flow pattern, the image signal of 256-gradation RGB for each pixel which is output from the color line CCD camera 16 is acquired by the image processor 18. On an image obtained from the image signal on which a process of enhancing a contrast is performed, whether the state of the flow pattern of the mold 12 is in the allowable range is visually confirmed.

In addition, for the purpose of simplification of the determination, the image signal of RGB is converted into the HSL color coordinate system by the conversion portion, and it can also be determined whether the shape (depth and inside diameter of the pore, pitch between the pores, or the like) of the fine concave-convex structure of the anodized alumina, the thickness of the anodized alumina, and the like is within a predetermined range based on digital information of the gradated hue (H).

In this case, on the image obtained from the image signal on which a process of enhancing a contrast is performed, whether the state of the flow pattern of the mold 12 is in the allowable range is visually confirmed.

Specifically, at the time of the determination, when NG pixels which are out of the range of gradation (threshold) of which the color gradation is set in advance are extracted, and the ratio of the NG pixels in a predetermined region (for example, 2,000×4,000 pixels) exceeds a predetermined ratio (for example, 5%), or the like, the mold 12 to be inspected is determined to be a defective product.

In the above-mentioned configuration, whether the flow pattern of the mold 12 is in the allowable range is visually confirmed. However, RGB of the obtained image signal or the average value of HSL is obtained, the image signal is scanned for each pixel in the transverse direction or the longitudinal direction, a variation along the average value is counted, and thus whether the flow pattern in the anodized alumina layer on the surface of the mold 12 is in the allowable range may be determined depending on whether the number of counts is within a predetermined range.

When the flow pattern is not present at all, the number of counts is 0. However, when the degree of the flow pattern is large, the number of counts increases due to an increase in the number of times along the average value.

In addition, Fourier transformation is performed on RGB of the obtained image signal or the HSL signal, and thus whether the flow pattern of the mold 12 is in the allowable range can also be determined depending on whether the strength of the frequency band within a predetermined range is within a predetermined range.

Additionally, a method of determining whether the flow pattern of the mold 12 is within a predetermined range is not limited to the above-mentioned methods.

In the method of manufacturing a mold according to the present invention, in addition to steps (a) to (e) mentioned above, a step of, as necessary, attaching a mold release agent to the surface of the anodized alumina (mold releasing step), a step of inspecting the attachment state of the mold release agent using the inspection device and the inspection method according to the present invention (mold release agent inspection step), and a step of, if desired, restoring the attachment state of the mold release agent (mold release agent restoration step) are performed.

The mold 12 determined to be a non-defective product (not to be a defective product) by the above-mentioned inspection is sent to the step of attaching the mold release agent to the surface of the anodized alumina (mold releasing step).

In the mold releasing step, mold releasing is performed on the surface on which the fine concave-convex structure of the mold is formed. The mold releasing method includes, for example, a method of coating silicon-based polymer or fluoropolymer, a method of evaporating a fluorine compound, a method of coating a fluorine-based or fluorine silicon-based silane compound, or the like.

The mold 12 in which the mold release agent is attached to the surface in this manner is sent to the mold release agent inspection step, and the attachment state of the mold release agent is inspected. The determination (mold release agent inspection step) of whether the attachment state of the mold release agent is within a predetermined range may be performed similarly to the inspection step of determining the quality of the fine concave-convex structure of the mold, using the inspection device of FIG. 1, and may be performed separately.

In the present embodiment, the mold 12 is irradiated with a linear ray of light from the irradiation device 14, the image of reflected light from the anodized alumina of the mold 12 is captured by the color line CCD camera 16, the image signal of 256-gradation RGB for each pixel which is output from the color line CCD camera 16 is acquired by the image processor 18, and the determination of the attachment condition of the mold release agent is performed based on the acquired image signal.

When each average value (average value after mold releasing) of RGB of the image signal (color information) from the color line CCD camera 16 is compared with each average value of RGB of the image signal (color information) before mold releasing, and the average value after mold releasing is within a predetermined threshold range with respect to the average value of RGB of the image signal before mold releasing, the attachment state of the mold release agent is determined to be a good state.

Alternatively, when the RGB image signal (color information) for each pixel of the anodized alumina which is output from the color line CCD camera 16 is set to the color (hue (H)) by conversion into the HSL color coordinate system, and before or after mold releasing, the value after mold releasing is within a predetermined threshold range with respect to the value before mold releasing as compared to this hue, the attachment state of the mold release agent may be determined to be a good state.

Further, the threshold which is set based on measurement data of a non-defective mold measured in advance is compared with the image signal after mold releasing of a mold to be inspected, and whether the attachment state of the mold release agent of the mold 12 to be inspected is appropriate may be determined.

In the above-mentioned mold release agent inspection step, the mold 12 of which the attachment state of the mold release agent is determined not to be good is sent to the mold release agent restoration step.

In the mold release agent restoration step, when an excessive amount of mold release agent is attached, the excess mold release agent is removed by cleaning or the like, and when the mold release agent lacks, mold releasing is performed again, and the mold release agent is added.

After that, the mold 12 is inspected again. The mold release agent inspection step and the mold release agent restoration step are repeated until the attachment state of the mold release agent is favorable.

EXAMPLES

Hereinafter, although the present invention is described in detail by way of examples, the present invention is not limited thereto.

(Mold a)

A discoid aluminum substrate (purity of 99.99%) having a diameter of 65 mm and a thickness of 2 mm was mirror-polished under the conditions in which arithmetic mean roughness Ra is less than or equal to 20 nm.

Step (a):

The above-mentioned aluminum substrate was anodized in an oxalic acid aqueous solution of 0.3 M for 30 minutes under the conditions of a direct current of 40 V and a temperature of 16° C.

Step (b):

The aluminum substrate on which an oxide film was formed was immersed in a mixed aqueous solution of 6% by mass phosphoric acid/1.8% by mass chromic acid, and the oxide film was removed.

Step (c):

The above-mentioned aluminum substrate was anodized in an oxalic acid aqueous solution of 0.3 M for 30 seconds under the conditions of a direct current of 40 V and a temperature of 16° C.

Step (d):

The aluminum substrate on which an oxide film was formed was immersed in a 5% by mass phosphoric acid aqueous solution of 30° C. for 8 minutes, and a pore diameter expansion was performed.

Step (e):

Step (c) and step (d) mentioned above were repeated 5 times in total, and a discoid mold a in which the anodized alumina with approximately conical pores having an average pitch of 100 nm and a depth of 200 nm was formed on the surface was obtained.

(Mold b)

A discoid mold b, in which anodized alumina with approximately conical pores having an average pitch of 100 nm and a depth of 100 nm was formed on the surface, was obtained in a similar manner to the manufacturing of the mold a, except that the time of anodization in the aforementioned step (c) was changed to 20 seconds.

(Mold c)

After fabric polishing was performed on a cylindrical aluminum substrate having no rolling trace obtained by cutting an aluminum ingot having a purity of 99.99% to an outside diameter of 200 mm, an inside diameter of 155 mm, and a length of 350 mm, this substrate was electro-polished in a mixed solution of perchloric acid/ethanol (volume ratio: ¼), and was mirror-finished.

Step (a):

The above-mentioned aluminum substrate was anodized in an oxalic acid aqueous solution of 0.3 M for 30 minutes under to conditions of a direct current of 40 V and a temperature of 16° C.

Step (b):

The aluminum substrate on which an oxide film having a thickness of 3 μm was formed was immersed in a mixed aqueous solution of 6% by mass phosphoric acid/1.8% by mass chromic acid, and the oxide film was removed.

Step (c):

The above-mentioned aluminum substrate was anodized in an oxalic acid aqueous solution of 0.3 M for 30 seconds under the conditions of a direct current of 40 V and a temperature of 16° C. At this time, agitation of the oxalic acid aqueous solution was stopped so that non-uniformity occurred in the temperature in the oxalic acid aqueous solution.

Step (d):

The aluminum substrate on which an oxide film was formed was immersed in a 5% by mass phosphoric acid aqueous solution of 30° C. for 8 minutes, and pore diameter expansion was performed.

Step (e):

Step (c) and step (d) mentioned above were repeated 5 times in total, and a roll-shaped mold c in which the anodized alumina with approximately conical pores having an average pitch of 100 nm and a depth of 200 nm on design was formed on the surface was obtained.

(Mold d)

A roll-shaped mold d in which the anodized alumina with approximately conical pores having an average pitch of 100 nm and a depth of 200 nm was formed on the surface was obtained similarly to the manufacturing of the mold c, except that agitation of the oxalic acid aqueous solution was perform so that non-uniformity did not occur in the temperature in oxalic acid aqueous solution in the aforementioned step (c).

(Mold e)

A roll-shaped mold e in which the anodized alumina with approximately conical pores having an average pitch of 100 nm and a depth of 200 nm was formed of the surface was obtained similarly to the manufacturing of the mold d except that a lot of the aluminum substrate is different.

Reference Example 1

The mold a was installed on the table so the surface on which the anodized alumina was formed was directed to the upper side, and an image of the surface of the anodized alumina was captured by a digital camera (IXY DIGITAL 55 manufactured by Cannon Inc.) from a place approximately 30 cm away. At this time, image capturing was performed so that the angle θ of the optical axis L of the digital camera was set to be approximately 70 degrees with respect to the normal line N of the surface (tangent plane) of the anodized alumina of the mold a.

As a result of image capturing, the surface of the anodized alumina with approximately conical pores having an average pitch of 100 nm and a depth of 200 nm (aspect ratio of 2) was confirmed to be light red.

Reference Example 2

The image of the surface of the anodized alumina was captured similarly to Reference Example 1, except that the mold a was changed to the mold b.

As a result of image capturing, the surface of the anodized alumina with approximately conical pores having an average pitch of 100 nm and a depth of 100 nm (aspect ratio of 1) was confirmed to be light green.

Example 1

The anodized alumina of the mold was inspected through the above-mentioned inspection method using the inspection device shown in FIG. 1.

The mold c was used as the mold 12.

As the linear illumination device 14, a fluorescent light source of FL20SS EX-N/18 manufactured by Panasonic Corporation was used at 40 kHz.

As the color line CCD camera 16, CV-L107CL-3CCD manufactured by JAI was used.

As the image processor 18, MIL9 manufactured by Matrox Electronic Systems Ltd. was used.

The color line CCD camera 16 imaged the angle θ of the optical axis L of the color line CCD camera 16 between 5 degrees and 85 degrees with respect to the normal line N of the surface (tangent plane) of the anodized alumina of the mold 12 which is in the imaging range, while changing the conditions.

The distance between the mold 12 and the color line CCD camera 16 was set to be approximately 50 cm.

The linear illumination device 14 was disposed so that reflected light entered the color line CCD camera 16.

Figure 4:
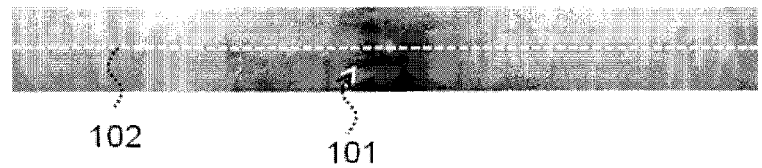
FIG. 4 is an image of a pore abnormal portion of the anodized alumina captured according to the present invention.

FIG. 4 is an image obtained by clipping a portion of an image in which a circumference of the surface of the anodized alumina of the mold 12 is captured under the conditions of angle θ=85 degrees of the optical axis L, and converting the color into monochrome.

An image of a pore abnormal portion 101 of the anodized alumina is captured in the vicinity of the center of the image and is shown as a dark portion.

Figure 5:
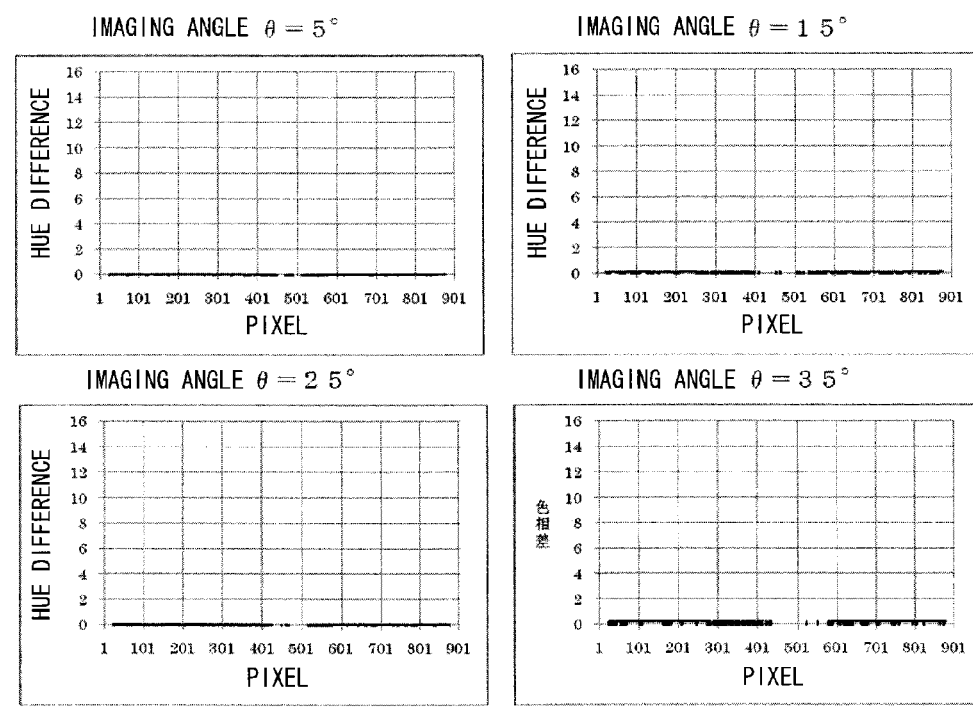
FIG. 5 is a diagram obtained by extracting one line of captured images for every 10 degrees between imaging angles of 5 degrees to 35 degrees.
Figure 6:
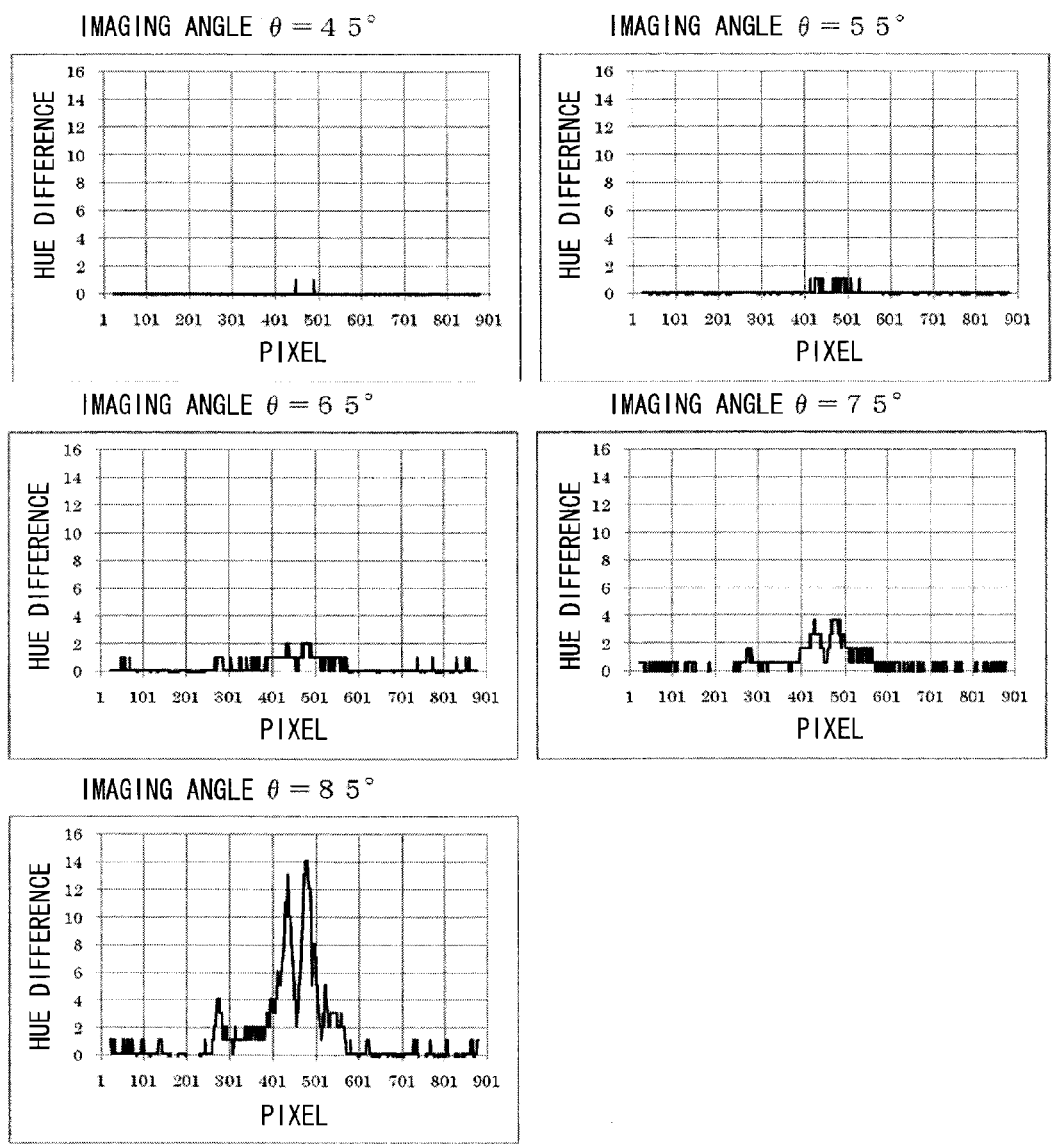
FIG. 6 is a diagram obtained by extracting one line of captured images for every 10 degrees between imaging angles of 45 degrees to 85 degrees.

FIGS. 5 and 6 show one-line data in which an image obtained by capturing the angle θ of the optical axis L every 10 degrees between 5 degrees and 85 degrees is converted from the RGB signal to the hue (H) signal by the image processor 18, and which includes the abnormal portion.

The hue (H) is normally expressed as 0 to 360 degrees, but 0 to 360 degrees are expressed as 8-bit data of 0 to 255 in the image processor 18.

The position of one-line data is one line shown by 102 of FIG. 4, and is also data located at the same position in an image captured at the angle θ of another optical axis L.

The vertical axis of each graph shown in FIGS. 5 and 6 is a value obtained by taking the difference from the hue (H) of the abnormal portion, based on the hue (H) of the normal portion. In addition, the horizontal axis thereof is a pixel.

For example, when the detection threshold is set to be greater than or equal to the hue difference of 1.0, the abnormal portion cannot be detected at angle θ=5 degrees to 35 degrees of the optical axis L in FIG. 5, and can be detected at angle θ=45 degrees or more of the optical axis L in FIG. 6. Therefore, as the angle θ of the optical axis L becomes larger, the detection sensitivity becomes higher.

Figure 7:
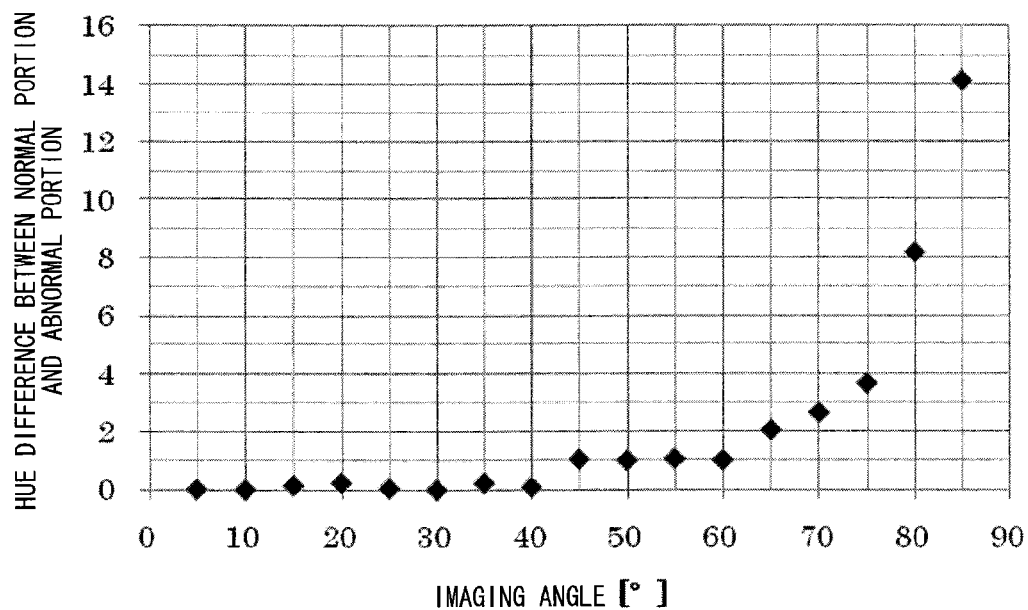
FIG. 7 is a diagram obtained by plotting the hue difference between a normal portion and an abnormal portion in each captured image for every 5 degrees between imaging angles of 5 degrees to 85 degrees.

FIG. 7 shows a result obtained by plotting the hue difference between the normal portion and the abnormal portion in each captured image for every 5 degrees between the imaging angles of 5 to 85 degrees.

Since the hue difference between the normal portion and the abnormal portion is larger than in the case of 45 degrees at angle θ=65 degrees of the optical axis L, the detection can be made with a good sensitivity. The detection sensitivity becomes higher at angle θ=80 degrees of the optical axis L, and thus the detection can be made with a better sensitivity at angle θ=85 degrees of the optical axis L in FIG. 7.

From the above-mentioned example, in order to carry out the present invention, the angle θ of the optical axis L of the color line CCD camera has to be set to be greater than or equal to 45 degrees with respect to the normal line N of the surface (tangent plane) of the anodized alumina of the mold which is in the imaging range, preferably greater than or equal to 65 degrees, more preferably greater than or equal to 80 degrees, and much more preferably greater than or equal to 85 degrees.

Example 2

The anodized alumina of the mold was inspected through the above-mentioned inspection method using the inspection device shown in FIG. 1.

The mold d was used as the mold 12.

As the linear illumination device 14, a fluorescent light source of FL20SS EX-N/18 manufactured by Panasonic Corporation was used at 40 kHz.

As the color line CCD camera 16, CV-L107CL-3CCD manufactured by JAI was used.

As the image processor 18, MIL9 manufactured by Matrox Electronic Systems Ltd. was used.

In the color line CCD camera 16, the angle θ of the optical axis L of the color line CCD camera 16 was set to 80 degrees with respect to the normal line N of the surface (tangent plane) of the anodized alumina of the mold 12 which is in the imaging range.

The distance between the mold 12 and the color line CCD camera 16 was set to be approximately 50 cm.

The linear illumination device 14 was disposed so that reflected light entered the color line CCD camera 16.

The image obtained by capturing a circumference of the surface of the anodized alumina of the mold 12 was converted from the RGB signal to the hue (H) signal of 8-bit data of 0 to 255 by the image processor 18.

The hue signal of a circumference of the surface of the anodized alumina was averaged throughout the entire image, and a pixel having a difference of more than 1.0 from the average value was set to an abnormal portion, but the abnormal portion was not detected in the mold 12.

As a result of creation of a transparent film having a fine concave-convex structure on the surface thereof using the mold 12, a uniform film could be created.

In addition, as a result of creation of a transparent film having a fine concave-convex structure on the surface thereof, for reference, similarly to the mold c used in Example 2, a non-uniform film was created.

Example 3

The attachment state of the mold release agent to the surface of the anodized alumina was inspected by the illumination device 14 (illumination means) and the color line CCD camera 16 (imaging means, or imaging device), using the inspection device shown in FIG. 1.

The mold d was used as the mold 12.

The illumination device 14, the color line CCD camera 16, and the image processor 18 are the same as those in Example 1.

Angle θ1 of an optical axis L1 of the color line CCD camera 16 with respect to a normal line N1 of the surface (tangent plane) of the anodized alumina of the mold d which is in the imaging range was set to 80 degrees.

The positional relationship between the mold d, and the color line CCD camera 16 and the illumination device 14 is the same as that in Example 1.

Figure 8:
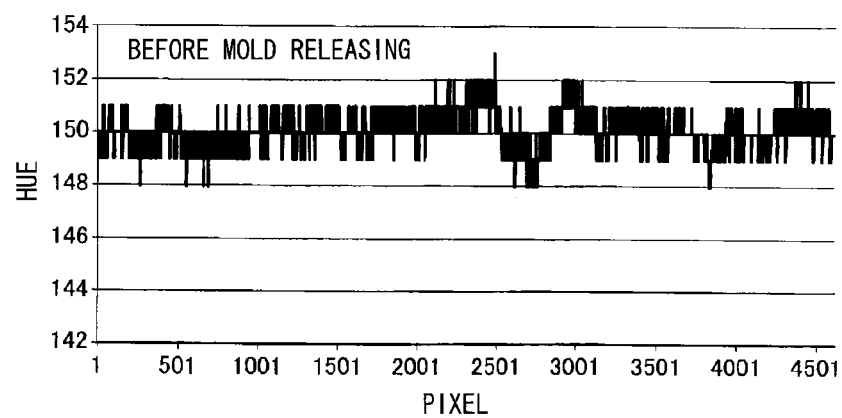
FIG. 8 is a graph illustrating a result obtained by capturing the mold before mold releasing using the inspection device of FIG. 1, performing conversion from an image signal of RGB to a hue (H) signal using an image processor, and extracting a circumference around the center of the mold in the longitudinal direction.

FIG. 8 is a diagram illustrating a result obtained by capturing a circumference of the surface of the mold in a state where mold releasing is not performed, performing conversion from the RGB image signal to the hue (H) signal using the image processor 18, and extracting a circumference around the center of the mold in the longitudinal direction.

Additionally, the hue (H) is normally expressed as 0 to 360 degrees, but 0 to 360 degrees are expressed as 8-bit data of 0 to 255 in the image processor 18.

Next, after the mold d was immersed for 10 minutes in a mold releasing solution prepared by dissolution in water using TDP-8 (manufactured by Nikko Chemicals Co., Ltd.) of 0.1% by mass, the mold was pulled up slow, mold releasing was performed by statically placing and drying the mold for more than 6 hours, and a mold d1 was obtained.

Figure 9:
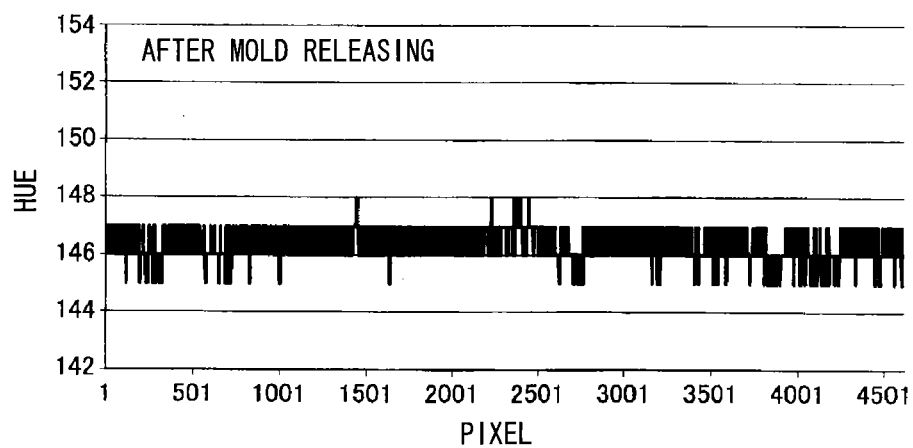
FIG. 9 is a graph illustrating a result obtained by capturing the mold after mold releasing using the inspection device of FIG. 1, performing conversion from an image signal of RGB to a hue (H) signal using the image processor, and extracting a circumference around the center of the mold in the longitudinal direction.

Again, the image of a circumference of the surface of the mold d1 was captured using the inspection device shown in FIG. 1. FIG. 9 is a diagram in which the imaging result is converted from the RGB image signal to the hue (H) signal using the image processor 18, and a circumference around the center of the mold in the longitudinal direction is extracted. The result is shown in FIG. 9.

The hue value is in the vicinity of 150 in FIG. 8 which is a result before mold releasing, but the hue value is changed to the vicinity of 146 in FIG. 9 after mold releasing.

Figure 11:
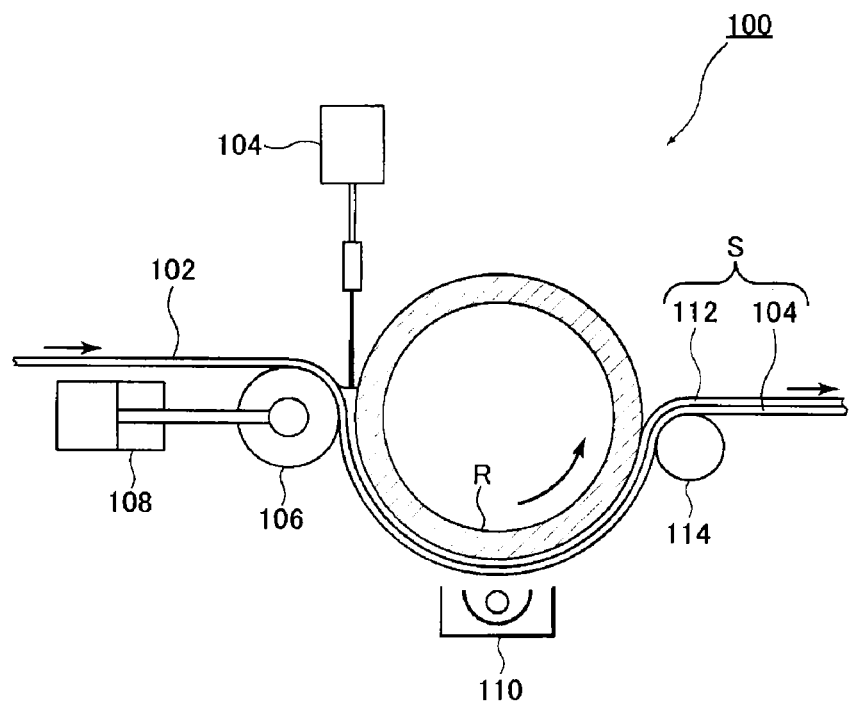
FIG. 11 is a schematic diagram illustrating an article manufacturing device into which the mold manufactured using a method of manufacturing a member having the anodized alumina of a preferred aspect of the present invention on the surface thereof is incorporated.

This mold was incorporated in a manufacturing device 100 of FIG. 11, and an elongated article S having a fine concave-convex structure on the surface thereof was manufactured.

The manufacturing device 100 of FIG. 11 includes a roll-shaped mold R, a tank 104 that supplies an active energy ray-curable resin composition between the roll-shaped mold R and a transparent substrate 102 moving along the surface of the lower half of the roll-shaped mold R in synchronization with the rotation of the mold R, a nip roll 106 that nips the transparent substrate 102 and the active energy ray-curable resin composition between the roll-shaped mold R and the nip roll, a pneumatic cylinder 108 that adjusts nip pressure of the nip roll 106, an active energy ray irradiation device 110, installed below the roll-shaped mold R, which irradiates the active energy ray-curable resin composition with an active energy ray through the transparent substrate 102, and a peeling roll 114 that peels the transparent substrate 102 having a curable resin layer 112 formed on the surface thereof from the roll-shaped mold R.

As a result of measurement of reflectance of the article having a fine concave-convex structure on the surface thereof immediately after the start of shaping, it is known that the fine concave-convex structure of the mold R is not properly transferred without obtaining a targeted value, and the attachment state of the mold release agent can be confirmed not to be good.

After the active energy ray-curable resin composition was disposed on the mold d1, and the resin composition was cured by ultraviolet irradiation, the resin composition was peeled from the mold d1, and the mold release agent attached to the mold was caused to transition to a cured material of the resin composition, the thereby obtain a mold d2 from which the attached mold release agent was removed.

Figure 10:
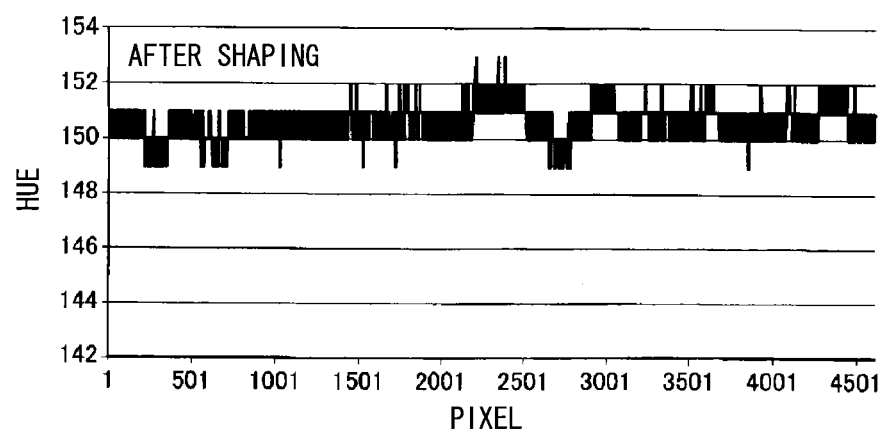
FIG. 10 is a graph illustrating a result obtained by capturing the mold after an attached mold release agent is removed using the inspection device of FIG. 1, performing conversion from an image signal of RGB to a hue (H) signal using the image processor, and extracting a circumference around the center of the mold in the longitudinal direction.

FIG. 10 shows a result of the inspection of the mold d2 using the inspection device shown in FIG. 1. As shown in FIG. 10, the hue value is in the vicinity of 150 before mold releasing in the mold d2, and there is a high possibility of the attachment state of the mold release agent being good.

The mold d2 was attached to the manufacturing device shown in FIG. 11, and an article having a fine concave-convex structure on the surface thereof was obtained. As a result of measurement of reflectance of the article, it was confirmed that an article having a targeted reflectance was obtained, the attachment of the mold release agent and the state of anodized alumina were all normal, and a desired article could be manufactured.

Example 4

The state of the flow pattern on the surface of the anodized alumina was inspected by the illumination device 14 (illumination means) and the color line CCD camera 16 (imaging means, or imaging device), using the inspection device shown in FIG. 1.

The mold e was used as the mold 12.

The illumination device 14, the color line CCD camera 16, and the image processor 18 are the same as those in Example 1.

The angle θ1 of the optical axis L1 of the color line CCD camera 16 with respect to the normal line N1 of the surface (tangent plane) of the anodized alumina of the mold e which is in the imaging range was set to 80 degrees.

The positional relationship between the mold e, and the color line CCD camera 16 and the illumination device 14 are the same as those in Example 1.

Figure 12:
FIG. 12 is an image of the surface of the mold having the anodized alumina on the surface thereof which is captured by imaging device.

FIG. 12 is an image which is obtained by clipping a portion of the image in which a circumference of the surface of the mold e is captured and converting the color into the monochrome and is capable of determining the state of the flow pattern of the mold. The flow pattern in the anodized alumina layer is captured throughout the entire image, and the degree of the flow pattern in the anodized alumina is confirmed to be out of the allowable range by visually observing this image.

Using the mold e, optical sheet S having a fine concave-convex structure on the surface thereof is manufactured using the manufacturing device 100 of FIG. 11.

Figure 13:
FIG. 13 is a captured image of an optical sheet having a fine concave-convex structure on the surface thereof.

FIG. 13 is an image obtained by capturing the optical sheet S having the manufactured fine concave-convex structure on the surface thereof using the line CCD, and clipping the portion corresponding to FIG. 12. Referring to FIG. 13, since an appearance defect of the flow pattern shape is present, it can be confirmed that the optical sheet S having the manufactured fine concave-convex structure on the surface thereof is a defective product, and that the flow pattern of the mold R causes the optical sheet S to be a defective product.

In addition, when FIG. 12 and FIG. 13 are compared with each other, light and darkness are reversed, but the flow patterns have the same shape. The anodized alumina inspection device and inspection method according to the present invention are used, so that the appearance defect of the flow pattern shape of the optical sheet S having a fine concave-convex structure on the surface thereof can be confirmed to be capable of being detected by inspecting the anodized alumina.

From the above-mentioned examples, it is possible to easily inspect the depth of the pores of the anodized alumina and the pitch between the pores through steps of inspecting the pore shape of the anodized alumina according to the present invention, and to manufacture the anodized alumina of which the pore shape is stable.

INDUSTRIAL APPLICABILITY

A method of manufacturing anodized alumina, and a method and device for inspecting the same according to the present invention are useful for manufacturing a mold in which the anodized alumina having two or more pores in which the pitch is less than or equal to the wavelength of visible light is formed on the surface, by anodizing the surface of an aluminum substrate.

DESCRIPTION OF THE REFERENCE SIGNS

12: mold
14: linear illumination device (illumination means)
16: color line CCD camera (imaging means, imaging device)
18: image processor (image processing means)
34: pore
35: oxide film (anodized alumina)
101: pore abnormal portion of anodized alumina

The invention claimed is:

1. A method of manufacturing an article having anodized alumina on a surface thereof, comprising: irradiating a surface of the article having anodized alumina with a structure having two or more pores in which a pore interval is less than or equal to a wavelength of visible light on the surface thereof and reflecting colored light, with light from an illumination device after the anodized alumina is formed; capturing an image of reflected colored light from the surface of the article having anodized alumina on the surface using an imaging device; acquiring color information from an image captured by the imaging device; and inspecting a shape of the pore of the article having anodized alumina on the surface based on the color information, wherein in the capturing the image of the reflected colored light from the surface of the article having anodized alumina on the surface using the imaging device, the imaging device having an optical axis at an angle of 45 to 89.9 degrees with respect to a normal line of the surface of anodized alumina.

2. The method of manufacturing an article having anodized alumina on the surface thereof according to claim 1, wherein in the capturing the image of the reflected light from the surface of the article having anodized alumina on the surface using the imaging device, the angle of the optical axis of the imaging device is 65 to 89.9 degrees with respect to the normal line of the surface of anodized alumina.

3. The method of manufacturing an article having anodized alumina on a surface thereof according to claim 1, wherein in the capturing the image of the reflected light from the surface of the article having anodized alumina on the surface using the imaging device, an angle of an optical axis of the imaging device is 80 to 89.9 degrees with respect to a normal line of the surface of anodized alumina.

4. The method of manufacturing an article having anodized alumina on a surface thereof according to claim 1, further comprising inspecting a mold release agent attached to a fine concave-convex structure on the surface of the article based on the color information.

5. The method of manufacturing an article having anodized alumina on a surface thereof according to claim 1, further comprising inspecting a flow pattern of the article having anodized alumina on the surface based on the color information.

6. The method of manufacturing an article having anodized alumina on a surface thereof according to claim 1, wherein the inspecting the shape of the pore of the article having anodized alumina on the surface based on the color information comprises
    capturing an image of reflected light from the surface of the article having anodized alumina on the surface as an RGB signal, and
    inspecting a shape of the pore of the article having anodized alumina on the surface based on information of the RGB signal.

7. The method of inspecting an anodized alumina according to claim 6, wherein in the capturing the image of the reflected light from the surface of the anodized alumina using the imaging device, the angle of the optical axis of the imaging device is 65 to 89.9 degrees with respect to the normal line of the surface of anodized alumina.

8. The method of inspecting an anodized alumina according to claim 6, wherein in the capturing the image of the reflected light from the surface of the anodized alumina using the imaging device, an angle of an optical axis of the imaging device is 80 to 89.9 degrees with respect to a normal line of the surface of the anodized alumina.

9. The method of inspecting an anodized alumina according to claim 6, wherein the determining whether the aspect ratio (depth/pitch) of the pore of the anodized alumina is within the predetermined range based on the color information, comprises,
  capturing an image of reflected light from the surface of the anodized alumina as an RGB signal, and
  inspecting a shape of the pore of the anodized alumina based on information of the RGB signal.

10. The method of manufacturing an article having anodized alumina on a surface thereof according to claim 1, wherein the inspecting the shape of the pore of the article having anodized alumina on the surface based on the color information comprises
  capturing reflected light from the surface of the article having anodized alumina on the surface as an alumina RGB signal,
  converting the RGB signal into an HSL color coordinate system, and
  inspecting a shape of the pore of the article having anodized alumina on the surface based on information of the HSL color coordinate system.

11. The method of manufacturing an article having anodized alumina on a surface thereof according to claim 1, further comprising following steps (a) to (e) before irradiating the surface of the article having anodized alumina on the surface thereof with light from the illumination device after the anodized alumina is formed:
  (a) a step of anodizing a surface of a mirror-finished aluminum substrate in an electrolyte at a constant voltage, and forming an oxide film on the surface;
  (b) a step of removing at least a portion of the oxide film, and forming a pore originating point of anodization on the surface of the aluminum substrate;
  (c) a step of re-anodizing the surface of the aluminum substrate, on which the pore originating point is formed, in an electrolyte at a constant voltage, and forming an oxide film having a pore corresponding to the pore originating point on the surface;
  (d) a step of expanding a diameter of the pore; and
  (e) a step of repeatedly performing the step (c) and the step (d).

12. A method of manufacturing an optical film, comprising transferring a fine concave-convex structure of the article manufactured by the manufacturing method according to claim 1 to manufacture the optical film.

13. A device of inspecting an article having anodized alumina on a surface thereof, comprising: an illumination device that irradiates the surface of the article having anodized alumina with a structure having two or more pores in which a pore interval is less than or equal to a wavelength of visible light on the surface and reflects colored light with light; an imaging device that captures an image of reflected colored light from the surface of the article having anodized alumina on the surface; and an image processor that determines whether an aspect ratio (depth/pitch) of the pore of the anodized alumina is within a predetermined range based on color information obtained from the image captured by the imaging device, wherein in the capturing the image of the reflected colored light from the surface of the article having anodized alumina on the surface using the imaging device, the imaging device having an optical axis at an angle of 45 to 89.9 degrees with respect to a normal line of the surface of anodized alumina.

14. The device of inspecting an article according to claim 13, wherein in the imaging device that captures an image of reflected light from the surface of the article having anodized alumina on the surface, an angle of an optical axis of the imaging device is 65 to 89.9 degrees with respect to a normal line of the surface of the anodized alumina.

15. The device of inspecting an article according to claim 13, wherein in the imaging device that captures an image of reflected light from the surface of the article having anodized alumina on the surface, an angle of an optical axis of the imaging device is 80 to 89.9 degrees with respect to a normal line of the surface of the anodized alumina.

16. The device of inspecting an article according to claim 13, wherein the image processor that inspects a shape of the pore based on the color information comprises
  imaging device for capturing an image of reflected light from the surface of the article having anodized alumina on the surface as an RGB signal, and
  inspecting device for inspecting a shape of the pore of the article having anodized alumina on the surface based on information of the RGB signal.

17. The device of inspecting an article according to claim 13, wherein the image processor inspects a mold release agent attached to a fine concave-convex structure on the surface of the article based on the color information.

18. The device of inspecting an article according to claim 13, wherein the image processor inspects a flow pattern of the article having a fine concave-convex structure on the surface of the article based on the color information.

19. A method of manufacturing an article having a fine concave-convex structure on a surface thereof, comprising: irradiating a surface of the article with the structure having two or more pores in which a pitch is less than or equal to a wavelength of visible light and reflecting colored light with light from an illumination device after the fine concave-convex structure is formed; capturing an image of reflected colored light from the surface of the article using an imaging device; acquiring color information from an image captured by the imaging device; and inspecting a shape of the fine concave-convex structure based on the color information, wherein in the capturing the image of the reflected colored light from the surface of the article having anodized alumina on the surface using the imaging device, the imaging device having an optical axis at an angle of 45 to 89.9 degrees with respect to a normal line of the surface of the fine concave-convex structure.

20. A method of inspecting an article having a fine concave-convex structure on a surface thereof, comprising: irradiating a surface of the article with the structure having two or more pores in which a pitch is less than or equal to a wavelength of visible light and reflecting colored light with light from an illumination device; capturing an image of reflected colored light from the surface of the article using an imaging device; acquiring color information from an image captured by the imaging device; and inspecting a shape of the fine concave-convex structure based on the color information, wherein in the capturing the image of the reflected colored light from the surface of the article having anodized alumina on the surface using the imaging device, the imaging device having an optical axis at an angle of 45 to 89.9 degrees with respect to a normal line of the surface of anodized alumina.

21. A method of inspecting an anodized alumina having two or more pores, comprising: irradiating a surface of the anodized alumina having two or more pores in which a pitch is less than or equal to a wavelength of visible light and reflecting colored light with light from an illumination device; capturing an image of reflected colored light from the surface of the anodized alumina using imaging device; acquiring color information from the image captured by the imaging device; and determining whether an aspect ratio (depth/pitch) of the pore of the anodized alumina is within a predetermined range based on the color information, wherein in the capturing the image of the reflected colored light from the surface of the article having anodized alumina on the surface using the imaging device, the imaging device having an optical axis at an angle of 45 to 89.9 degrees with respect to a normal line of the surface of anodized alumina.

* * * * *